United States Patent [19]

Liang et al.

[11] Patent Number: 5,062,708

[45] Date of Patent: Nov. 5, 1991

[54] CAPACITIVELY COUPLED PLASMA DETECTOR FOR GAS CHROMATOGRAPHY

[75] Inventors: Dong C. Liang, Vancouver; Michael W. Blades, Surrey, both of Canada

[73] Assignee: University of British Columbia, Vancouver, Canada

[21] Appl. No.: 354,150

[22] Filed: May 19, 1989

[51] Int. Cl.$^5$ .......................................... G01N 21/73
[52] U.S. Cl. ............................. 356/316; 315/111.21
[58] Field of Search ....................................... 356/316

[56] References Cited

U.S. PATENT DOCUMENTS 4,479,075  10/1984  Elliott ........................... 356/316 X

FOREIGN PATENT DOCUMENTS 2183087  5/1987  United Kingdom .

OTHER PUBLICATIONS

A. J. McCormack et al., Sensitive Selective Gas Chromatography Detector Based on Emission Spectrometry of Organic Compounds, Anal. Chem., 1965, 37, 1470.
C. A. Bache et al., Determination of Organophosphorus Insecticide Residues Using the Emission Spectrometric Detector, Anal. Chem., 1965, 37, 1477.
C. A. Bache et al., Determination of Iodinated Herbicide Residues and Metabolites by Gas Chromatography Using the Emission Spectrometric Detector, Anal. Chem., 1966, 38, 783.
C. A. Bache et al., Low Pressure Emission Spectrometric Determination of Part-Per-Billion Residue Levels of Organophosphorus Insecticides, Anal. Chem., 1966, 38, 1757.
C. A. Bache et al., Selective Emission Spectrometric Determination of Nanogram Quantities of Organic Bromine, Chlorine, Iodine, Phosphorus, and Sulfur Compounds in a Helium Plasma, Anal. Chem., 1967, 39, 786.
C. I. M. Beenakker, A Cavity for Microwave-Induced Plasmas Operated in Helium and Argon at Atmospheric Pressure, Spectrochim. Acta., Part B, 1976, 31B, 483.
C. I. M. Beenakker et al, Additional Experience with the Cylindrical TM010 Cavity for Generating an MIP in Helium and Argon at Atmospheric Pressure, Spectrochim. Acta., 1978, 33B, 56.
R. J. Lloyd et al., Direct Current Atmospheric Pressure Argon Plasma Emission Echelle Spectrometer as a Specific Metal Gas Chromatographic Detector, Anal Chem., 1978, 50, 2025.
Robert B. Costanzo et al., Alternating Current Plasma Detector for Selective Mercury Detection in Gas Chromatograph, Anal Chem., 1988, 60, 826.
Peter C. Uden et al., Determination of Methylcyclopentadienylmanganesetricarbonyl in Gasoline by Gas Chromatography with Interfaced Direct Current Argon Plasma Emission Detection, Anal. Chem., 1978, 50, 852.
Robert S. Braman et al., Direct Current Discharge Spectral Emission-Type Detector, Anal Chem., 1968, 40, 95.
David L. Windsor et al., Evaluation of Inductively Coupled Plasma Optical Emission Spectrometry as a Method for the Elemental Analysis of Organic Compounds, Applied Spectroscopy, 1978, 32, 366.
Robert B. Costanzo et al., Simlex Optimization of the Alternating-Current Plasma Detector for Gas Chromatography, Applied Spectroscopy, 1988, 42, 1387.
D. C. Liang et al., Atmospheric Pressure Capacitively Coupled Plasma Atomizer for Atomic Absorption Spectrometry, Anal Chem., 1988, 60, 27.
C. I. M. Beenakker, Evaluation of a Microwave-Induced Plasma in Helium at Atmospheric Pressure as an Element-Selective Detector for Gas Chromatography, Spectrochimica Acta, 1977, 32B, 173.
Scott A. Estes et al., Microwave-Excited Atmospheric Pressure Helium Plasma Emission Detection Characteristics in Fused Silica Capillary Gas Chromatography, Anal. Chem., 1981, 53, 1829.

Primary Examiner—Vincent P. McGraw
Attorney, Agent, or Firm—Barrigar & Oyen

[57] ABSTRACT

This invention pertains to a novel plasma detector that is useful for the detection of compounds separated by gas chromatography. More particularly, the invention relates to a novel radio-frequency, atmospheric pressure capacitively coupled plasma torch which can be used as an element specific, spectroscopic detector for gas chromatography. A method of detecting compounds separated by gas chromatography comprising passing the gas product of a gas chromatograph through a radio-frequency atmospheric pressure capacitively coupled plasma and anaylzing the results.

13 Claims, 4 Drawing Sheets

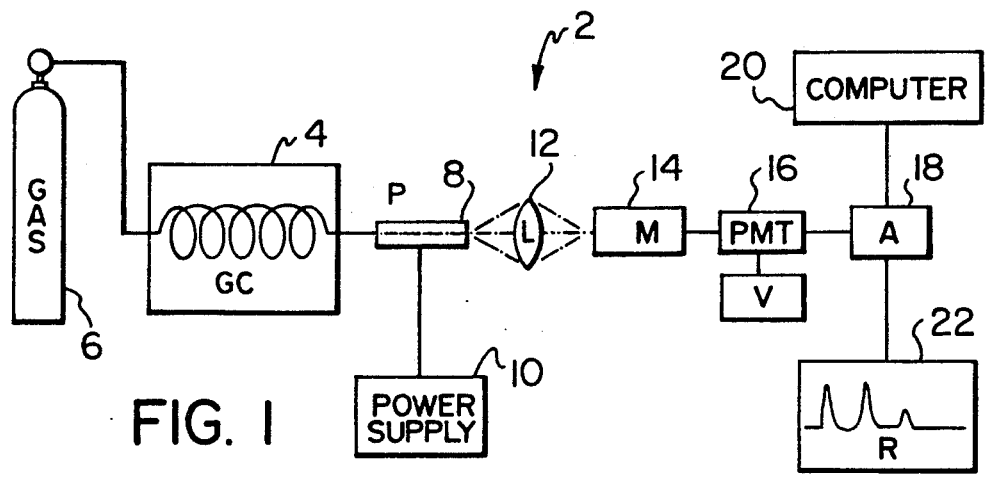
FIG. 1
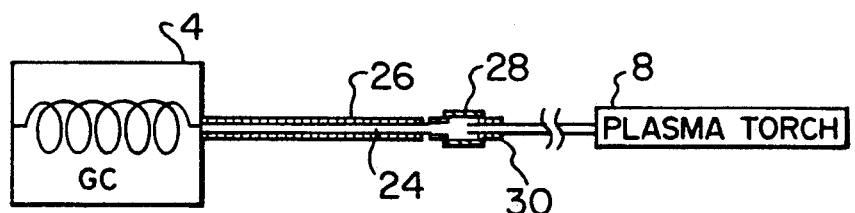
FIG. 2
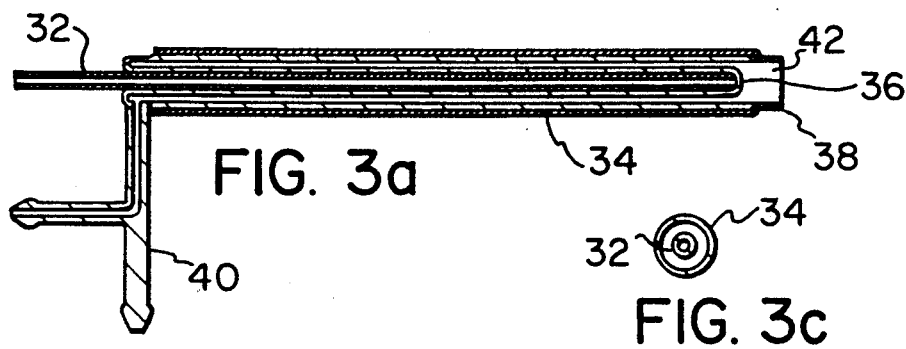
FIG. 3a
FIG. 3c
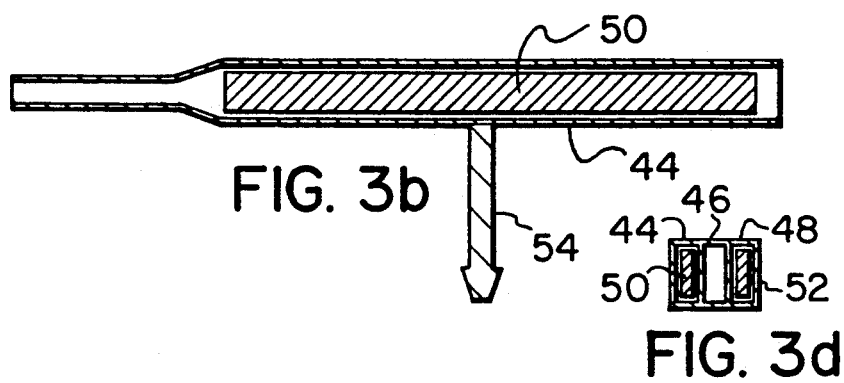
FIG. 3b
FIG. 3d

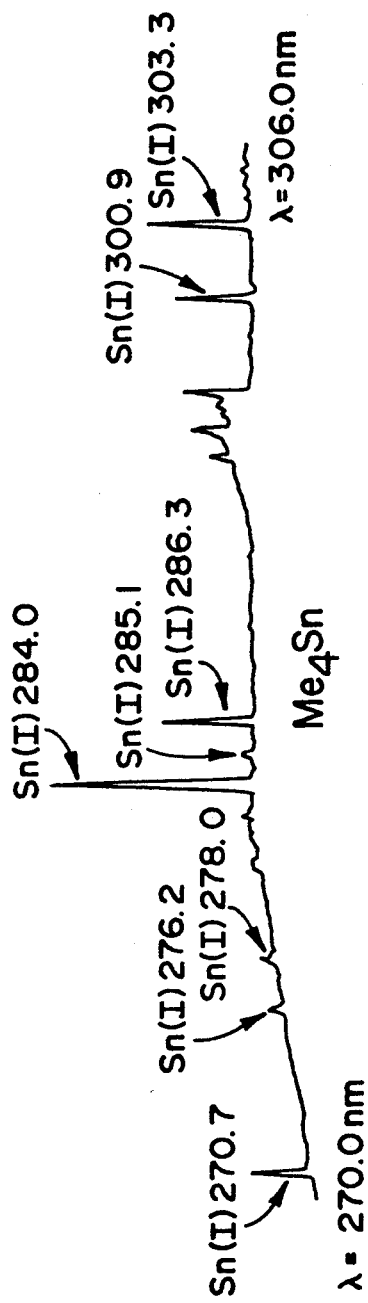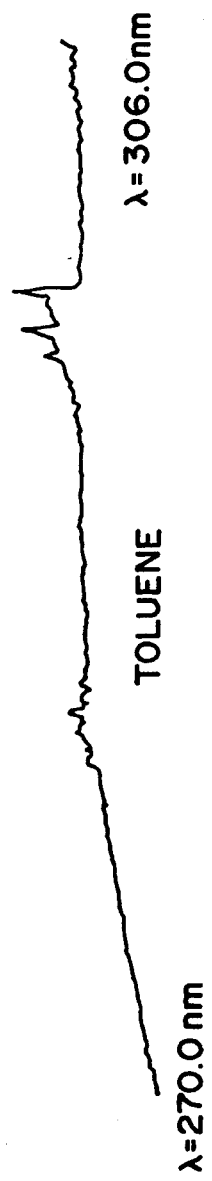
FIG. 4a
FIG. 4b

CAPACITIVELY COUPLED PLASMA DETECTOR FOR GAS CHROMATOGRAPHY

CROSS REFERENCE

The patent application assigned Ser. No. 07/354,511 entitled "Furnace Atomization Atmospheric Pressure Capacitively Coupled Plasma Excitation Source" filed on May 19, 1989 in the names of the same inventors as this application discloses subject matter common to this application.

FIELD OF THE INVENTION

This invention pertains to a novel plasma detector that is useful for the detection of compounds separated by gas chromatography. More particularly, the invention relates to a novel radio-frequency, atmospheric pressure capacitively coupled plasma torch which can be used as an element specific, spectroscopic detector for gas chromatography.

BACKGROUND OF THE INVENTION

Atomic emission spectroscopic detectors for gas chromatography have become an important analytical methodology because they simplify the interpretation of complex chromatograms by providing element specific information about each eluting peak. Plasma sources play an important role in this field. A. J. McCormack, S. C. Tong, and W. D. Cooke, published an article Anal. Chem., 1965, 37, 1470, based on plasma emission spectroscopy. Since that time, several kinds of plasmas, including microwave induced plasmas (MIP), direct current plasmas (DCP), alternating current plasmas (ACP), and inductively coupled plasmas (ICP) have been utilized as gas chromatography detectors. The MIP has been the most successful because a relatively low power is required to sustain the plasma, a relatively small quantity of gas is consumed during routine operation and the detector volume can be kept small.

In initial work using a MIP as a gas chromatography detector, McCormach et al. used a 2450 MHz, atmospheric pressure argon,discharge to detect the elution of halogen and other non-metal containing compounds. The detection limits for most of the non-metal elements were found to be in the range of $10^{-12}$ to $10^{-9}$ g/s. C. A. Bache and D. J. Lisk, Anal. Chem., 1965, 37, 1477; C. A. Bache and D. J. Lisk, Anal. Chem., 1966, 38, 783; C. A. Bache and D. J. Lisk, Anal. Chem., 1966, 38, 1757 and C. A. Bache and D. J. Lisk, Anal. Chem., 1967, 39, 786 used a helium MIP at low pressure (5-10 mm Hg) and found that better power coupling and hence better atomization characteristics could be obtained. This situation was improved with the development of the C.I.M. Beenakker, Spectrochim. Acta., Part B, 1976, 31B, 483 TM010 cylindrical resonance cavity which allowed efficient power coupling to an MIP at atmospheric pressure and at a relatively low power level (40-100 w).

Although the MIP is an excellent excitation source for element specific gas chromatography detection its use is constrained by some operational limitations. MIP cavities must be resonant with the driving frequency. According to C.I.M. Beenakker, and P.J.W.M. Boumans, Spectrochim. Acta., 1978, 33B, 56, coupling of power using a fixed loop as originally described by Beenakker is adequate for a helium plasma but not for an argon plasma. Additionally, discharge conditions in MIP depend both on the inner diameter of the cavity and the dielectrics inside the cavity. An MIP is normally ignited using a Tesla discharge.

U.K. Patent No. 2,183,087 A discloses a method and apparatus to produce a noble-gas plasma for excitation in optical emission spectrometry. The apparatus includes an hf generator 8 feeding operating at the resonant frequency of an oscillation circuit 1 consisting of at least one inductor L and one capacitor C1. The capacitor includes at least two capacitor plates 10, 11 which are so shaped and mutually arranged that they enclose a cavity 12 in which the plasma may form. A sensor (22, FIG. 9) may detect the magnetic field and a regulating circuit 17 may adjust the capacitance of a second capacitor C2 in parallel with capacitor C2 to tune the oscillator circuit to the desired frequency, particularly during start up. This patent shows a electrode formed of a pair of facing semi-circular plates 12 (See FIGS. 1 and 2) which generate a short length plasma which thus has little sensitivity. No operating or analytical data is disclosed to confirm the viability and functionality of the method and apparatus.

SUMMARY OF THE INVENTION

The inventions pertains to a method of detecting compounds separated by gas chromatography comprising passing the eluant of a gas chromatograph through a radio-frequency atmospheric pressure capacitively coupled plasma and analyzing the results.

The power supply to the plasma operates at between about 10 and 500 watts. The radio-frequency can be between about 200 KHz to 60 MHz. The support gas product flow rate can be about 5 to 100 mL/m.

In the method, the capacitively coupled plasma can be used to detect both inorganic and organic compounds in the fluent phase. The method can be used to detect both atomic and molecule spectral.

The invention is also directed to an apparatus for spectroscopic detection of the eluant of a gas chromatograph which comprises: (a) a capacitively coupled plasma torch powered by a power supply; (b) a spectrometer; (c) a lens for focusing the light from the plasma torch to the spectrometer; (d) a photomultiplier tube connected to the spectrometer; (e) a digital data acquisition computer connected to the photomultiplier tube and adapted to receive the signal from the photomultiplier; and (f) an analog-digital converter for recording the results of the digital data acquisition.

In the apparatus, the plasma torch has electrodes which can be concentric to one another and are planar and arranged parallel to one another.

Alternatively, the plasma torch can be a quartz tube which has a tubular electrode concentrically disposed on the outside thereof and a smaller tubular electrode disposed in the center of the quartz tube and separated from the plasma cavity in the tube. The plasma torch can be constructed of three adjacent parallel disposed hollow rectangular-cross section quartz tubes arranged adjacent to and parallel with one another, and a first planar electrode can be disposed within one of the exterior quartz tubes and a second planar electrode can be disposed within the opposite exterior quartz tube, leaving the middle quartz tube hollow for containing the plasma.

DRAWINGS

In drawings which illustrate specific embodiments of the invention but which should not be construed as restricting the spirit or scope of the invention in any way:

FIG. 1 is a schematic diagram of an apparatus for using capacitively coupled plasma as a gas chromatography detector;

FIG. 2 is a detail schematic diagram of the interface of a gas chromatograph column with a plasma torch;

FIG. 3a is a schematic diagram of a capacitively coupled plasma torch with concentric geometry;

FIG. 3b is a schematic diagram of a capacitively coupled plasma torch with parallel plate planar geometry;

FIG. 3c and 3d are end views of the diagrams of FIGS. 3a and 3b, respectively;

FIGS. 4a and 4b are a capacitively coupled plasma emission spectrum of $(CH_3)_4Sn$ detected using a concentric geometry Ar CCP, against a background spectrum of Toluene, respectively, between 270 and 306 nm. at power: 100 W; Frequency: 200 KHz; Carrier gas flow: 30 mL/m.

Figure 5A:
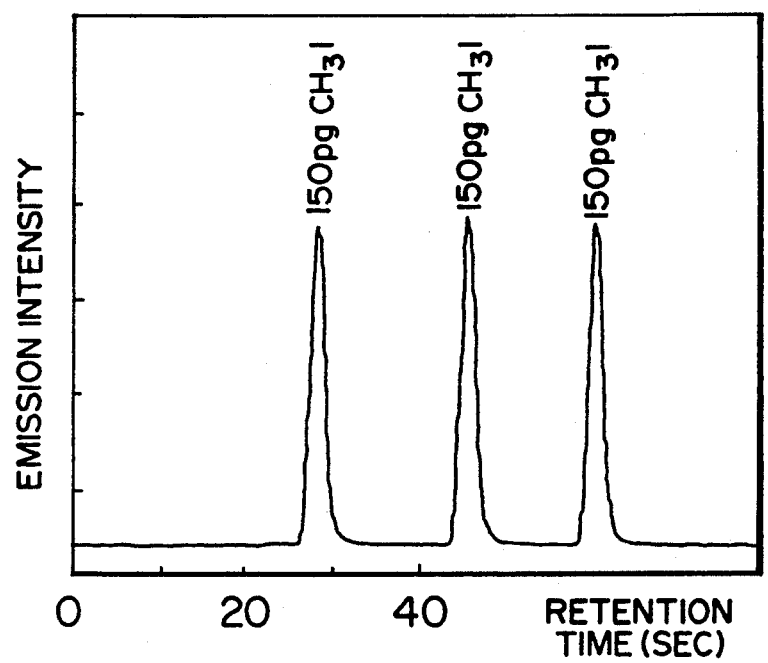
Figure 5B:
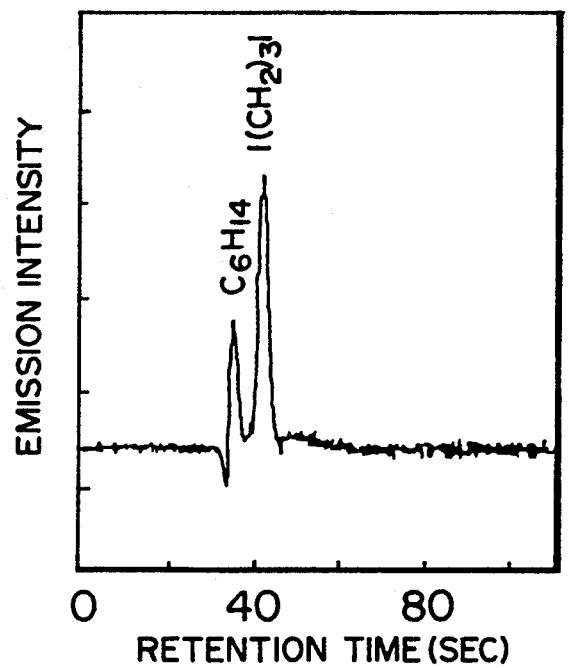
Figure 6A:
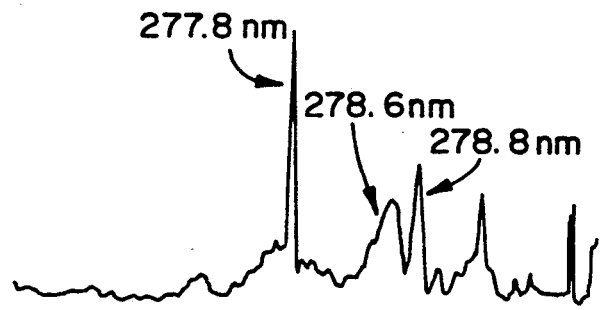
Figure 6B:
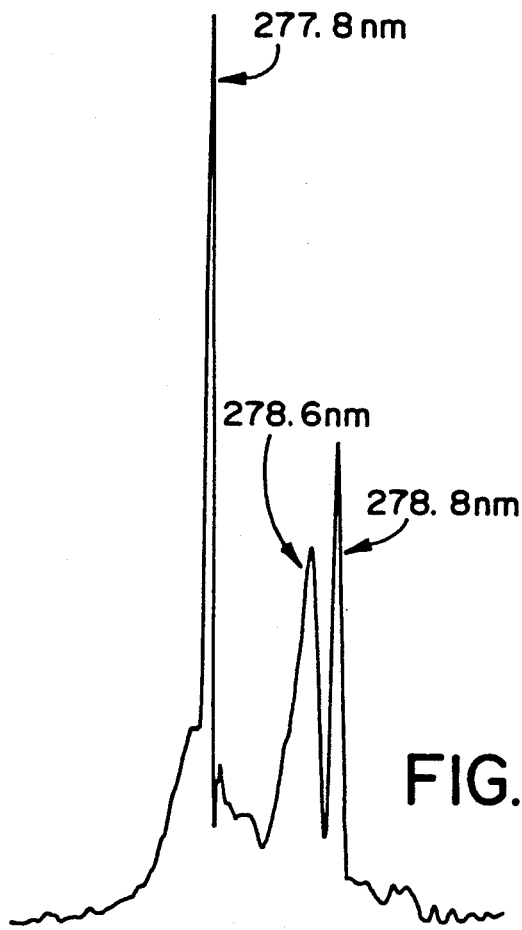

FIG. 5a illustrates gas chromatograms obtained for three replicate injections of 150 pg of iodomethane $\{CH_3I\}$ into a gas chromatograph; and FIG. 5b illustrates a gas chromatogram of 0.1 μL of 0.1 ppm di-iodopropane $\{(CH_2)_3I_2\}$ in hexane detected using a capacitively coupled plasma;

FIGS. 6a and b show the spectra of C-Cl band in Ar(a) and He(b) plasmas respectively.

DETAILED DESCRIPTION OF SPECIFIC EMBODIMENTS OF THE INVENTION

FIG. 1 illustrates a schematic diagram of an atmospheric pressure capacitively coupled plasma torch which can be used as an element specific, spectroscopic detector for gas chromatography. The plasma torch is made relatively small to reduce peak broadening and to enhance sensitivity for gas chromatograph detection. Using the torch of the invention, we have determined that a stable self-igniting plasma can be sustained over a wide range of operating frequencies, input powers, and at very low carrier gas flow rates. The major advantages of the torch of the invention over a MIP is that the discharge can be sustained over a very wide range of conditions; power from 10 to 500 W, frequency from 200 KHz to 30 MHz, and carrier gas flow rates as low as 20 mL/m. In addition, the torch configuration is simple, the plasma is stable, and a separate ignition system is not required.

As seen in FIG. 1, the radio-frequency atmospheric pressure capacitively coupled plasma gas chromatograph 2 comprises a gas chromatograph 4 which at its inlet end is supplied with gas 6 and at its outlet end is connected to a plasma torch 8. The plasma torch 8 is powered by power supply 10. The light from the plasma torch is transmitted through a focusing lens 12 into a monochromator 14. The monochromator 14 is connected to a photo-multiplier tube (PMT) high voltage power supply 16, which in turn is connected to an amplifier 18. The signal from the amplifier 18 is acquired and stored by a computer 20 and recorded by a chart recorder 22 simultaneously. Details of the components depicted in FIG. 1 are outlined in Table 1.

TABLE 1

| Experimental Facilities and Operating Conditions | |
|---|---|
| Gas Chromatograph | Varian 6000 Gas Chromatograph Columns: OV-101 and OV-07 Carrier gas flow rate: 30–80 ml/m |

TABLE 1-continued

| Experimental Facilities and Operating Conditions | |
|---|---|
| Plasma Power Supply | (a) Perkin-Elmer ICP 5500 system consisting of a Plasma-Therm (Kreeson, N.J.), HFP-2500F RF generator, AMN-2500 E automatic matching network, APCS-3 automatic power control system and PF2500 torch box (b) ENI power systems Inc. (Rochester, N,Y,), Model HPG-2 RF power supply; frequency 125–375 KHz, output power 0–200 W |
| Spectrometer | Schoffel-McPherson (Acton, MA) Model 270, 0.35 Czerny-Turner mount scanning monochromator with 1200 lines/mm holographic grating, reciprocal linear dispersion of 2nm/mm in the first order, entrance and exit slits set to 50 μm |
| Detector electronics | The photocurrent from a Hammatsu R955 photomultiplier tube was amplified by an amplifier made by the inventors. The photomultiplier tube was powered by a McPherson Model EU-42A PMT power supply. |
| Data Acquisition | Digital data acquisition: Zenith computer, Model W-248-82, (512 K, Zenith Electronics Corp.), IBM-AT compatible computer equipped with a RC Electronics (Santa Barbara, CA) Model ISC-16 analog-digital converter running the RC computerscope software package. Analog data recording: Fisher Recordall 5000 chart recorder. |

Specifically the outlet of the gas chromatograph column 4 was connected to the gas inlet of the capacitively coupled plasma torch 8 through a 1 M length of 1.5 mm i.d. Cu tubing which was maintained at a slightly higher temperature than the gas chromatography column using heating tape (Electrothermal Engineering Ltd.), which surrounded the interface tubing. Details of this interface are illustrated in more detail in FIG. 2. As seen in FIG. 2, the outlet of the gas chromatograph 4 was connected to a copper tube 24 which was wrapped in heating tape 26. The outlet of the copper tube 24 was connected to a copper fitting 28 which had teflon tape 30 connecting the fitting 28 to the inlet of the plasma torch 8.

Two different plasma discharge geometries have been used. Schematic diagrams for each of these are provided in FIGS. 3a and 3b, and end views are shown in FIGS. 3c and 3d, respectively. FIG. 3a shows a concentric design which is made from a single piece of quartz. The electrodes 32 and 34 which couple the rf power from the power supply 10 into the discharge are arranged concentrically in that the inner electrode 32 is housed inside a hollow quartz shaft 36 which is sealed such that there is no electrode contact with the plasma. The outer electrode 34 is a stainless steel cylinder which is wrapped around the outside of the quartz tube 38 in the manner shown in FIG. 3a. The entire apparatus is supported by support arm 40. When rf power from the power supply 10 is applied, the generated plasma fills the annular space between the electrodes 32 and 34 as well as the small space 42 at the end of the torch.

The second geometry depicted in FIG. 3b consists of three rectangular quartz tubes 44, 46 and 48 each of which has a dimension 2 mm by 4 mm. The central tube 46 contains the plasma and is sandwiched between the two quartz tubes 44 and 48, each of which encloses a stainless steel electrode 50 and 52 of slightly smaller dimensions than the interior dimensions of the respective quartz tubes 44 and 48. Carrier gas from the gas chromatography column is directed into the plasma through the inlet end of the torch. A B5 joint tube 54 serves as support but does not act to introduce any extra flow of gas.

Analytical Procedure

The spectra of organic compounds tested were obtained by using a 200 mL plastic bottle as a sample diluting container, in which the carrier gas was mixed with the injected volatile organic compounds and introduced to the plasma. Using this apparatus, a continuous flow of volatile compound could be introduced into the plasma so that emission spectra could be obtained. After selection of an appropriate analysis line, the wavelength was fixed, the bottle was removed, and the gas chromatography interface was arranged as depicted in FIG. 2 so that the gas chromatograph eluent could be introduced to the plasma discharge.

When operating at 27.12 MHz, it was found that energy was lost through heat radiation more easily in the concentric electrode torch (FIG. 3a and 3c) than the planar, parallel plate torch (FIG. 3b and 3d). This is probably because turbulence is much more prevalent in the cylindrical shape of torch. Also, it was found that when the input power was increased, the discharge in the concentric electrode torch became unstable. Both argon and helium gases were used in this work. It was found that the helium plasma was more suitable for identifying non-metal elements, for example, I, Cl and Br; whereas metal elements for example Sn, gave much larger responses in argon plasma. While the inventors do not wish to be bound by any theories, it is possible that there are some selective energy transfer processes between excited He and the non-metals which are not operative for metals such as Sn. As a consequence, helium was used when non-metal elements were being detected while argon was used when metal elements were being detected.

To show that it is feasible to use the capacitively coupled plasma torch to dissociate organic compounds and excite the atoms, trimethyl tin ($Me_4Sn$) was continuously introduced into the concentric plasma. The tin (Sn) emission spectrum from $Me < Sn$ between 270 and 306 nm is reproduced in FIG. 4a. A toluene background spectrum is provided in FIG. 4b for reference. The rf input power was 100 W at 200 KHz and the carrier gas flow was 30 mL/m. The presence of Sn I lines indicates that this capacitively coupled plasma torch is an effective dissociation and excitation source.

From FIG. 4a and 4b, it can be seen that the solvent (hexane) also gave a response because of an increase in background emission. This problem could probably be overcome with background correction by using a polychromator or a multichannel photodiode array instead of a single channel PMT detector 16.

The $3\sigma$ detection limit for the gas chromatography determination I in $I(CH_2)_3I$ was determined to be $8.2 \times 10^{-14}$ g/s.

FIGS. 5a and 5b depict the emission spectrometric gas chromatograms of iodomethane ($CH_3I$)(FIG. 5a) and 1, 3-diiodopropane ($I(CH_2)_3I$) {FIG. 5b} solution in hexane. The planar parallel electrode plasma (FIG. 3b) was operated at an input power of 50 W at a frequency of 27.18 MHz and a gas chromatograph carrier gas flow rate of 30 mL/m. The monochromator 14 was fixed at the iodine 206.2 nm line. The column temperature for $CH_3I$ and $I(CH_2)_3I$ were 90° C. and 120° C. respectively. The injector block temperature was maintained 20° C. higher than the oven temperature in each case. The interface transfer line temperature was maintained at 10° C. above the column temperatures. The $CH_3I$ was injected as the headspace vapor, whereas $I(CH_2)_3I$ was injected as a solution.

FIGS. 6a and b show the spectra of C-Cl band in Ar(a) and He(b) plasmas respectively. The rf input power was 80 W at 27.12 MHz and the gas flow rate was 80 mL/m. With these conditions the chlorine atomic lines have not been found. However, at higher power supply, for example 150 W, the chlorine atomic or ionic lines (e.g. 479.5 nm, 481.0 nm, 481.9 nm) could be obtained.

We can get both atomic and molecular spectra from the CCP-GC Detector. From the molecular spectra we can obtain molecular structure information.

The invention provides very effective energy transfer from a power supply to a plasma by capacitive coupling. We have demonstrated that a He or Ar plasma can be generated at atmospheric pressure at any frequency between 0.20 and at least 27.18 MHz. The advantages of the capacitively coupled plasma when compared with the MIP are its relatively simple construction, ease of ignition, flexibility in choice of operating conditions (rf power and frequency) and flexible geometry.

The main advantages of the capacitively coupled plasma detector are listed as follows:

Low detection limit ($8.2 \times 10^{-14}$ g/ for iodine);
(2) Element-specific information;
(3) Simplification of the interpretation of complex chromatograms;
(4) Multi-element capability;
(5) Both qualitative and quantitative information provided for selected elements;
(6) Effective energy transfer in capacitively coupled plasma allows a discharge to be sustained over a very wide range of conditions;
(7) No resonant cavity is required (the shape of the plasma torch is flexible);
(8) Relatively heavy solvent-loading possible compared to microwave induced plasma (MIP); and
(9) Separate plasma-ignition system not required.

The invention has utility as a tool for organic and inorganic analysis and should compete with existent gas detectors such as TCD, FID, NPD, ECD, and MIP-OED. The device can be widely used in industrial, chemical, environmental, pharmaceutical, biomedical, government, and research laboratories.

The device of the invention can replace existing technology in existing gas chromatographs or can be incorporated into new gas chromatographs. The device can improve on existing devices for carrying out element-specific detection in gas chromatography.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A method of spectroscopically investigating compounds separated in the eluant of a gas chromatograph comprising the steps of:
   passing the eluant of the gas chromatograph into a radio-frequency atmospheric pressure capacitively coupled plasma created between a pair of opposing electrically conducting electrodes;

applying radio-frequency power from a power supply to the electrodes sufficient to create a plasma in the eluant passing between the electrodes; and analyzing the light spectrum emitted from the plasma.

2. A method as claimed in claim 1 wherein a power supply to the plasma operates at between about 10 and 500 watts.

3. A method as claimed in claim 1 wherein the radio-frequency is between about 200 KHz to 60 MHz.

4. A method as claimed in claim 1 wherein the eluant gas flow rate is about 5 to 100 mL/m.

5. A method as claimed in claim 1 wherein the capacitively coupled plasma is used to detect both inorganic and organic compounds in the eluant phase.

6. A method as claimed in claim 5 wherein an atomic or molecular spectra is deleted.

7. A method as claimed in claim 1 including the steps of:
 (a) focusing the light from the plasma to a spectrometer by utilizing a lens;
 (b) detecting the data from the spectrometer by utilizing a photomultiplier tube;
 (c) transmitting a signal generated by the photomultiplier tube to a digital data acquisition computer connected to the photomultiplier tube; and
 (d) recording the results of the digital data acquisition utilizing an analog-digital converter.

8. An apparatus for spectroscopic detection comprising:
 (a) a gas chromatograph for outputting eluant;
 (b) a capacitively coupled plasma torch having a pair of opposing electrically conductive electrodes and adapted for receiving the eluant from the gas chromatograph and for passing the eluant between the electrodes;
 (c) means for applying a radio-frequency field between the electrodes to create a plasma in the eluant;
 (d) a spectrometer for analyzing light from the plasma torch;
 (e) a lens for focusing the light from the plasma torch to the spectrometer;
 (f) a photomultiplier tube connected to the spectrometer;
 (g) a digital data acquisition computer connected to the photomultiplier tube and adapted to receive an output signal from the photomultiplier; and
 (h) an analog-digital converter for recording the results of the digital data acquisition.

9. An apparatus as claimed in claim 8 wherein the electrodes are concentric to one another.

10. An apparatus as claimed in claim 8 wherein the electrodes are planar and arranged parallel to one another.

11. An apparatus as claimed in claim 9 wherein the plasma torch is a quartz tube and the electrodes comprise a tubular electrode concentrically disposed on the outside thereof and a smaller tubular electrode disposed in the center of the quartz tube and separated from the plasma cavity in the tube.

12. An apparatus as claimed in claim 10 wherein the plasma torch is constructed of three adjacent parallel disposed hollow rectangular-cross section quartz tubes, arranged adjacent to and parallel with one another, and the electrodes comprise a first planar electrode disposed within one of the exterior quartz tubes and a second planar electrode disposed within the opposite exterior quartz tube, and the middle quartz tube is hollow for containing the plasma.

13. A method for the spectroscopic investigation of the eluant from a gas chromatograph comprising the steps of:
 (a) passing a stream of gas between two opposing electrically conducting electrodes;
 (b) applying radio-frequency power to the electrodes to thereby maintain a gas plasma between the electrodes;
 (c) introducing eluant from the gas chromatograph into the gas plasma; and
 (d) examining the light spectrum emitted from the plasma.

* * * * *